(12) United States Patent
Dougan et al.

(10) Patent No.: US 7,059,334 B2
(45) Date of Patent: Jun. 13, 2006

(54) DENTAL FLOSS DEVICE

(75) Inventors: Michael Dougan, Dublin (IE); Paul Sullivan, Dublin (IE); Conor Kennedy, Dublin (IE)

(73) Assignee: APC Limited, Dublin (IE)

( * ) Notice: Subject to any disclaimer, the term of this patent is extended or adjusted under 35 U.S.C. 154(b) by 296 days.

(21) Appl. No.: 10/301,599

(22) Filed: Nov. 22, 2002

(65) Prior Publication Data

US 2003/0098037 A1     May 29, 2003

Related U.S. Application Data

(60) Provisional application No. 60/332,010, filed on Nov. 23, 2001.

(51) Int. Cl.
*A61C 15/00* (2006.01)

(52) U.S. Cl. .................................................... 132/323

(58) Field of Classification Search ......... 132/323–327
See application file for complete search history.

(56) References Cited

U.S. PATENT DOCUMENTS

| | | | |
|---|---|---|---|
| 3,892,249 A | 7/1975 | Jones et al. | 132/89 |
| 3,926,201 A | 12/1975 | Katz | 132/91 |
| 3,927,686 A | 12/1975 | Zambito | 132/91 |
| 4,006,750 A | 2/1977 | Chodorow | 132/91 |
| 4,051,857 A * | 10/1977 | Zambito | 132/323 |
| 4,192,330 A | 3/1980 | Johnson | 132/91 |
| 5,010,906 A * | 4/1991 | Preciutti | 132/323 |
| 5,056,540 A | 10/1991 | Page | 132/323 |
| 5,125,424 A * | 6/1992 | Eisen | 132/323 |
| 5,127,415 A | 7/1992 | Preciutti | 132/323 |
| 5,170,809 A | 12/1992 | Imai et al. | 132/322 |
| 5,261,430 A * | 11/1993 | Mochel | 132/322 |
| 5,388,600 A | 2/1995 | Hart | 132/323 |
| 5,483,982 A | 1/1996 | Bennett et al. | 132/323 |
| 5,538,023 A | 7/1996 | Oczkowski et al. | 132/323 |
| 5,579,786 A | 12/1996 | Wolk et al. | 132/322 |
| 5,738,124 A | 4/1998 | Cervato | 132/323 |
| D497,222 S * | 10/2004 | Ochs et al. | D28/68 |

FOREIGN PATENT DOCUMENTS

| | | |
|---|---|---|
| DE | 8708369.8 | 10/1987 |
| EP | 0904744 A2 | 3/1999 |
| WO | WO00/44302 | 8/2000 |
| WO | WO02/32341 | 4/2002 |

* cited by examiner

*Primary Examiner*—Kevin Shaver
*Assistant Examiner*—Stephanie Willatt
(74) *Attorney, Agent, or Firm*—Jacobson Holman PLLC

(57) ABSTRACT

A dental floss device includes a handle having a head piece and a disposable holder for a length of dental floss. The holder includes a base portion and a pair of spaced-apart jaws extending from the base and which extend to embrace the head piece of the handle when the holder is in a correct alignment configuration with respect to the handle. The device has an interlock which ensures that the holder can be interengaged with the head piece only when the holder is correctly aligned with the head piece. The interlock includes a head interlock part provided by interlock grooves and a holder interlock part provided by corresponding interlock tongues. There are two interlock grooves and corresponding interlock tongues which slidably interengage when the holder is correctly aligned with the head piece. If the holder is turned so that it is not correctly aligned with the head piece, the interlock tongues of the holder prevent engagement of the holder with the head piece. Thus there is no risk that a user will incorrectly align and engage the dental floss holder with the head piece.

14 Claims, 7 Drawing Sheets

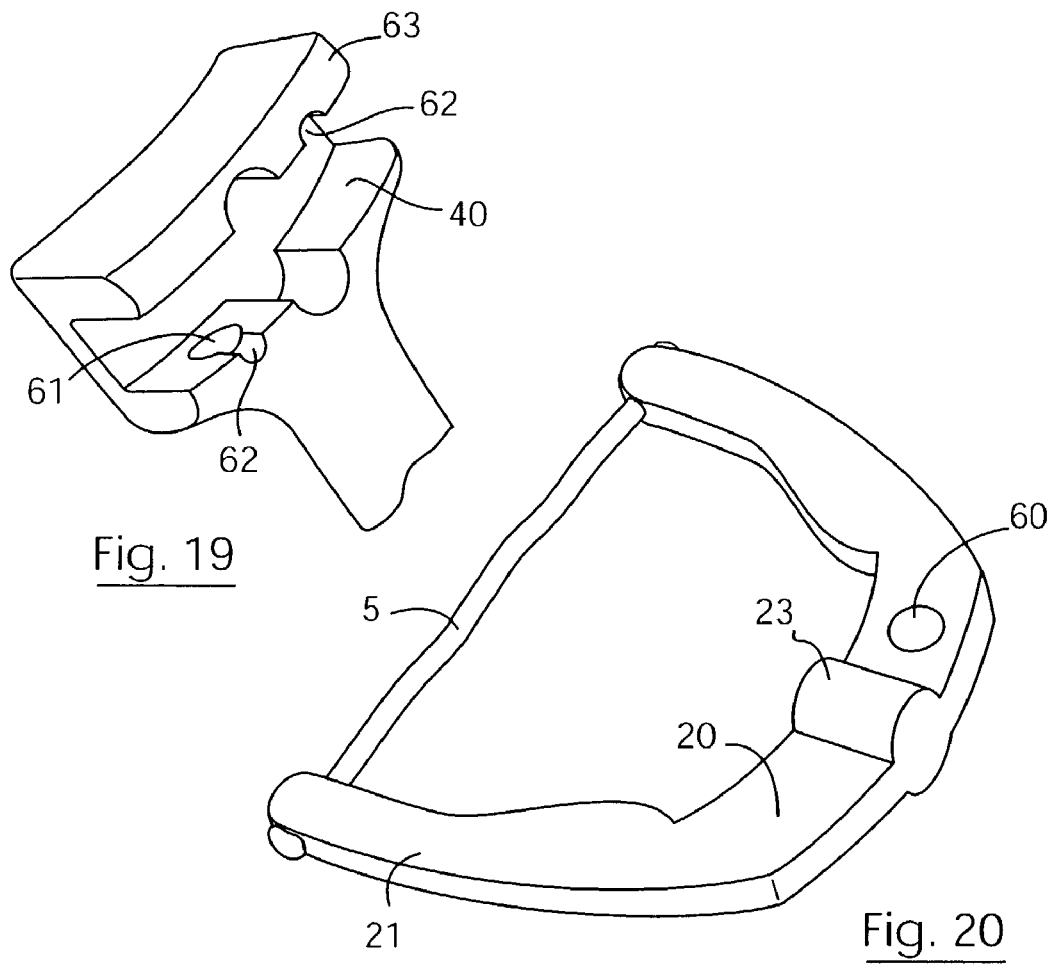
Fig. 19
Fig. 20
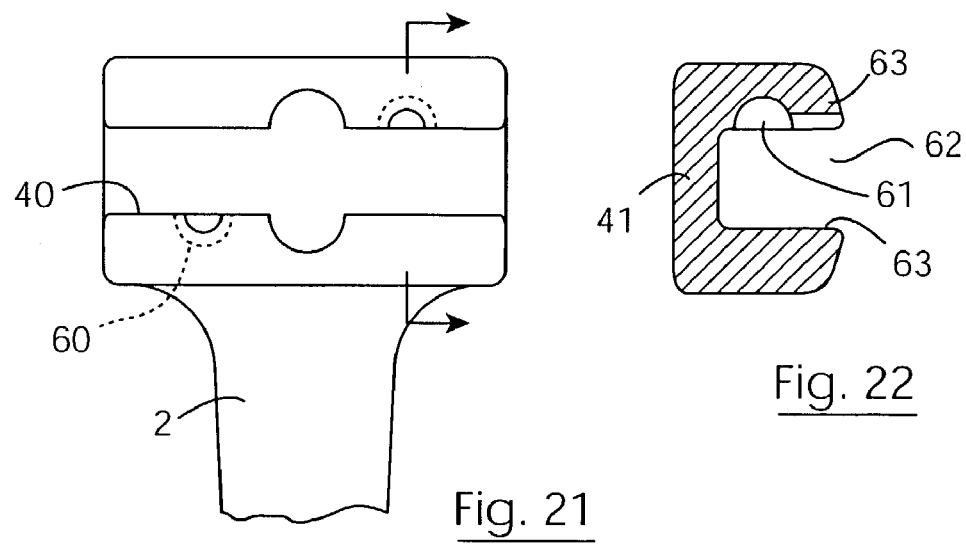
Fig. 21
Fig. 22

DENTAL FLOSS DEVICE

This is a complete application claiming benefit of provisional 60/332,010 filed Nov. 23, 2001.

INTRODUCTION

The invention relates to a dental floss device of the type comprising a disposable dental floss holder for interengagement with a head piece of a handle, on assembly.

Conventional dental floss devices of this type suffer from the disadvantage that there is a risk that a user may not correctly interengage the holder with the head piece of the handle. This leads to inefficient flossing as the floss position is not optimised. There is also a risk that the holder may move and/or become dislodged in use.

There is therefore a need for an improved dental floss device which will address these issues.

STATEMENTS OF INVENTION

According to the invention there is provided a dental floss device comprising:
 a handle having a head piece; and
 a dental floss holder for inter-engagement with the head piece;
 the dental floss holder comprising a base portion and a pair of spaced-apart jaws extending from the base portion to accommodate a length of dental floss therebetween;
 the jaws of the holder extending to embrace the head piece therebetween in a correct alignment configuration of the holder with respect to the handle; and an interlock to substantially prevent inter-engagement of the holder with the head piece except when the holder is in the correct alignment configuration.

In one embodiment the interlock comprises a head interlock part on the head piece and a holder interlock part on the dental floss holder, the interlock parts being adapted to inter-engage only when the holder is in the correct alignment configuration.

Preferably the interlock parts comprise a projection and a recess to receive the projection.

Most preferably the interlock parts are a push fit when the holder is in the correct alignment configuration.

In one embodiment the interlock parts comprise an interlock tongue and a corresponding interlock groove to receive the interlock tongue. Preferably the interlock tongue is slidably engagable in the interlock groove when the holder is correctly aligned with the head piece. Advantageously the interlock tongue is of arcuate shape in cross section and the interlock groove is of complementary arcuate shape.

In one embodiment the interlock comprises a single head interlock part and a single holder interlock part.

In another embodiment the interlock comprises at least two head interlock parts on the head piece and at least two holder interlock parts on the dental floss holder.

In one embodiment of the invention the device comprises a transversely extending engagement groove on the holder or head piece and a complementary engagement tongue portion on the other of the holder or head piece which engages the transversely extending engagement groove, on assembly of the holder and head piece.

Preferably the interlock comprises a head interlock part and a corresponding holder interlock part, the head interlock part being provided on one of the engagement tongue or engagement groove and the corresponding holder interlock part being provided on the other of the engagement tongue or engagement groove.

Preferably the interlock part extends laterally of the engagement tongue or engagement groove.

In one embodiment the dental floss holder comprises a releasable lock for engagement on assembly with the head piece. Preferably the releasable lock comprises snap fit projections.

Most preferably the snap fit projections are provided on the jaws of the holder.

In one embodiment the dental floss is a length of dental floss string.

In another embodiment the dental floss is a length of dental floss tape.

The invention also provides a handle for a dental floss device of the invention.

The invention further provides a dental floss holder for assembly to a head piece of a handle, the dental floss holder comprising a base portion and a pair of spaced-apart jaws extending from the base portion to accommodate a length of dental floss therebetween the jaws of the holder extending to embrace a head piece of a handle therebetween in a correct alignment configuration of the holder with respect to a handle, in use, the dental floss holder having a holder interlock to substantially prevent inter-engagement of the holder with a head piece except when the holder is in a correct alignment configuration.

Preferably the holder interlock comprises an interlock projection or an interlock recess for engagement, on assembly with a corresponding interlock tongue or interlock recess of a head piece only when the holder is in the correct alignment configuration. Most preferably the interlock projection comprises an interlock tongue. Preferably the interlock recess comprises an interlock groove.

Preferably the interlock tongue or the interlock groove extends from the base portion of the holder

BRIEF DESCRIPTION OF THE DRAWINGS

The invention will be more clearly understood from the following description thereof given by way of example only with reference to the accompanying drawings, in which:

FIG. 19 is a side perspective view of the handle head piece part of the device of FIG. 14;

FIG. 20 is a side perspective view of the holder part of the device of FIG. 14;

FIG. 21 is an end perspective view of the handle head piece part of the device of FIG. 14; and FIG. 22 is a cross sectional view of the handle head piece of FIG. 21 along the line indicated in FIG. 21.

DETAILED DESCRIPTION

Figures 1, 2:
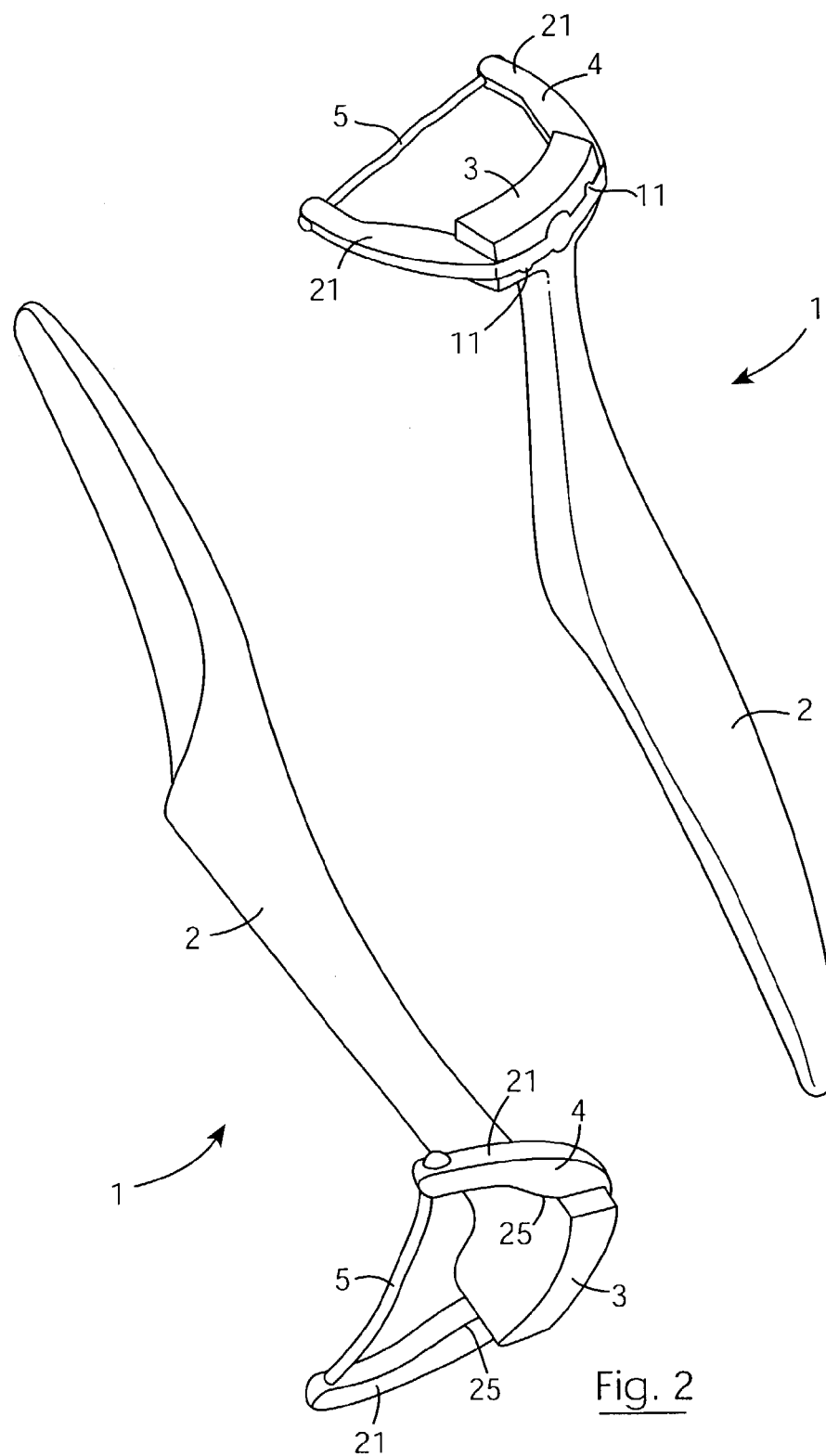
FIG. 1 is a perspective view of an assembled dental floss device of the invention.
FIG. 2 is another perspective view of the device.
Figure 3B:
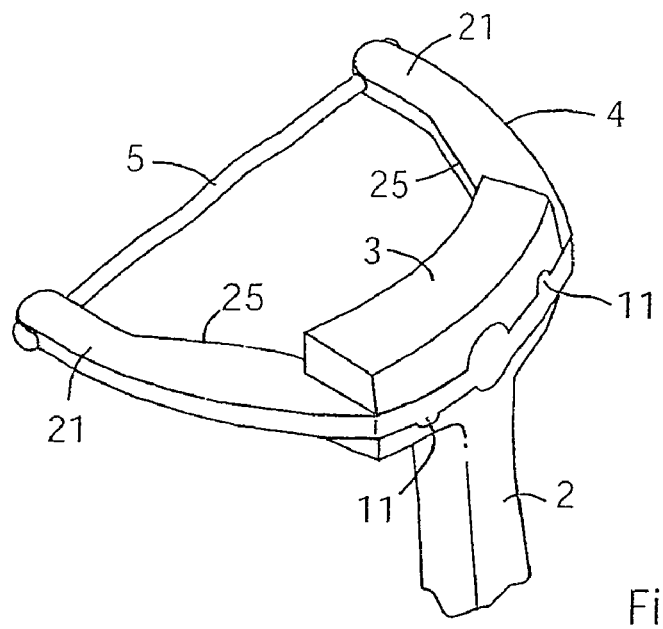
FIGS. 3(a) and 3(b) are perspective views illustrating the assembly of a dental floss holder part and a handle head piece part of the device.
Figure 3A:
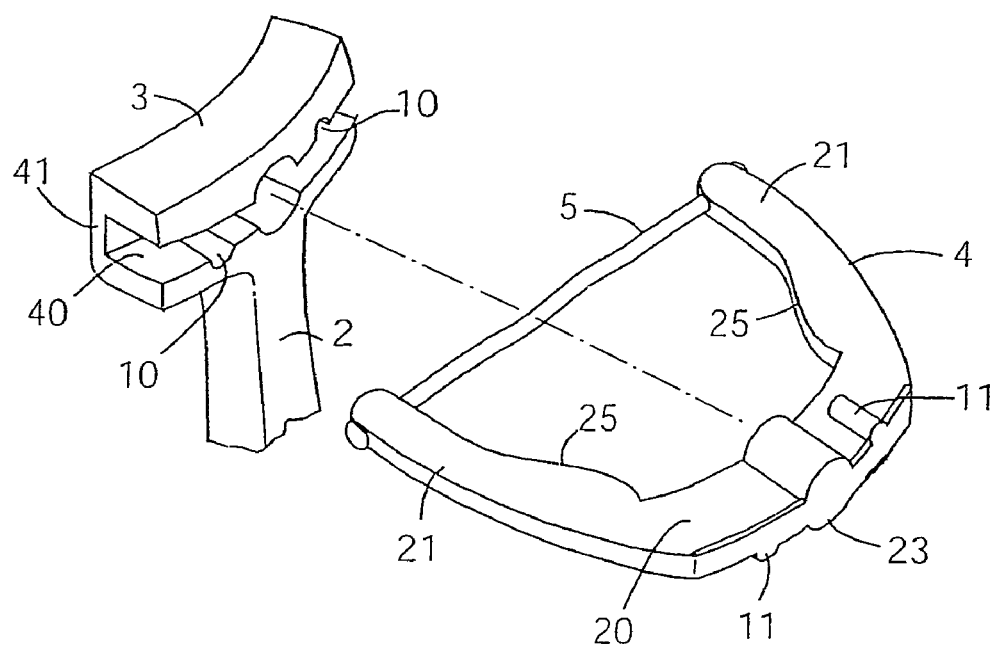
Figure 5:
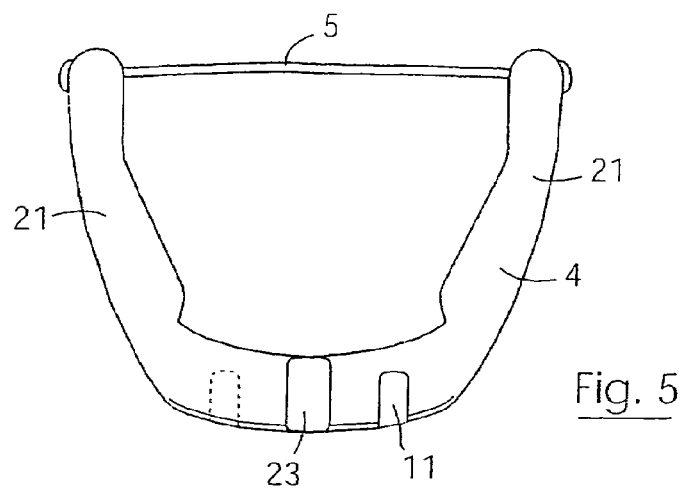
FIG. 5 is a top plan view of the holder of FIG. 4.
Figure 6:
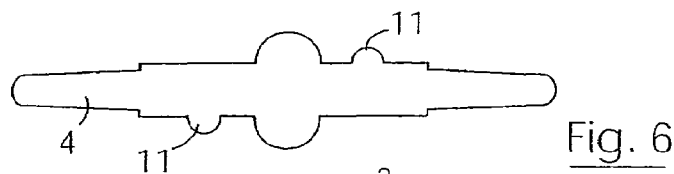
FIG. 6 is an end view of the holder of FIG. 4.
Figure 7:
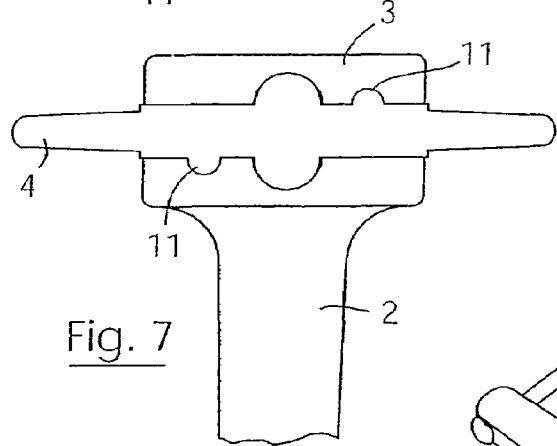
FIG. 7 is an end view of the holder mounted to a head piece.
Figure 4:
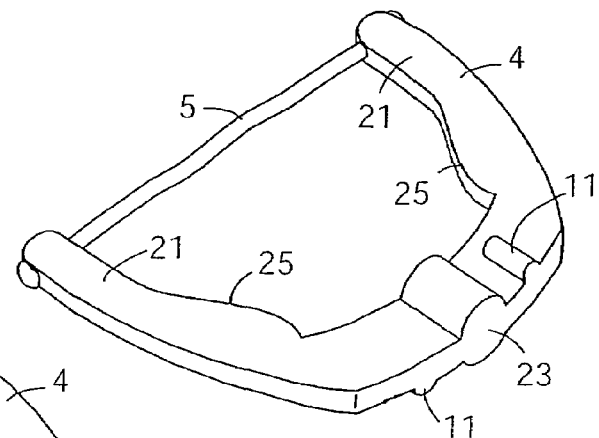
FIG. 4 is a perspective view of a dental floss holder according to the invention.

Referring to the drawings and initially to FIGS. 1 to 7 thereof there is illustrated a dental floss device 1 according to the invention comprising a handle 2 having a head piece 3 and a disposable holder 4 for a length of dental floss 5. The device has an interlock which ensures that the holder 4 can be interengaged with the head piece 3 only when the holder 4 is correctly orientated and aligned with the head piece 3, as illustrated. The interlock comprises a head interlock part provided by interlock grooves 10 and a holder interlock part provided by corresponding interlock tongues 11. In this case, there are two interlock grooves 10 and corresponding interlock tongues 11 which slidably interengage when the holder 4 is correctly aligned with the head piece 3. If the holder 4 is turned so that it is not correctly aligned with the head piece 3, the interlock tongues 11 of the holder 4 prevent engagement of the holder 4 with the head piece 3. Thus there is no risk that a user will incorrectly align and engage the dental floss holder 4 with the head piece 3.

In more detail, the holder 4 comprises a base portion 20 which in this case is of arcuate shape in longitudinal cross section and a pair of spaced-apart jaws 21 extending from the base portion 20 to accommodate a length of floss 5 therebetween. The base portion 20 includes an enlarged central section 23 and interlock tongue 11 extends laterally of the base portion 20. In this case there are two interlock tongues 11 which extend from opposite sides of the base portion 20. The jaws 21 each have inwardly extending snap fit projections 25.

The correct alignment configuration of the holder is, as illustrated, when the jaws 21 of the holder extend to embrace the head piece therebetween. An incorrect alignment of the holder to the head piece would be if a user positioned the holder such that the jaws did not embrace the head piece but rather extended away from it.

The handle 2 is shaped and contoured for ease of holding and use by a user. The head piece 3 has a transversely extending engagement groove 40 which is of complementary arcuate shape to that of the base portion 20 of the holder 4. In effect, the base portion 20 of the holder 4 forms an engagement tongue which is releasably engaged, on assembly, in the engagement groove 40 of the head piece 3 of the handle 2.

The head piece 3 also has an end or floor section 41 over which the snap projections 25 of the holder 4 pass and behind which the snap projections 25 engage, an assembly. In this way the holder 4 is securely engaged with the head piece 3.

In use, the holder 4 is fitted to the head piece 3 by first inserting the head piece through the gap defined between the jaws 21 and floss length 5 of the holder 4. The base portion or engagement tongue 20 is then correctly aligned with the engagement groove 40 and the interlock tongues 11 and grooves 10 are also aligned. The holder 4 is then pressed using light pressure to snap fittingly engage the projections 25 behind the floor 41 of the head piece 3. To release the holder 4 from the head piece 3 finger pressure is used to reverse the procedure by first disengaging the snap projections 25 from behind the floor 41 of the head piece 3. The spent holder 4 can then be disposed of and replaced by a fresh holder 4.

Figure 8:
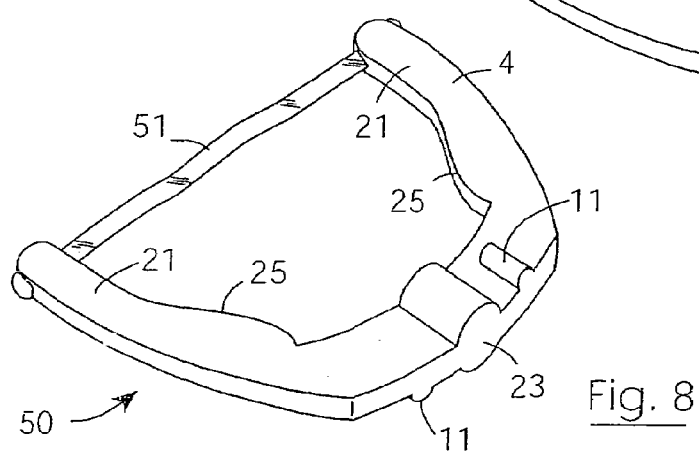
FIG. 8 is a perspective view of another holder of the invention.
Figure 9B:
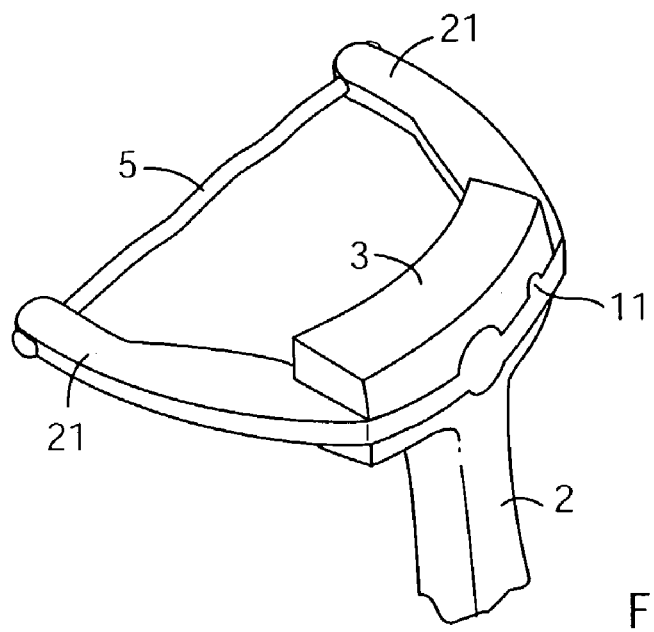
FIGS. 9(a) and 9(b) are perspective views illustrating the assembly of a dental floss holder part and a handle head piece part of another dental floss device of the invention.
Figure 9A:
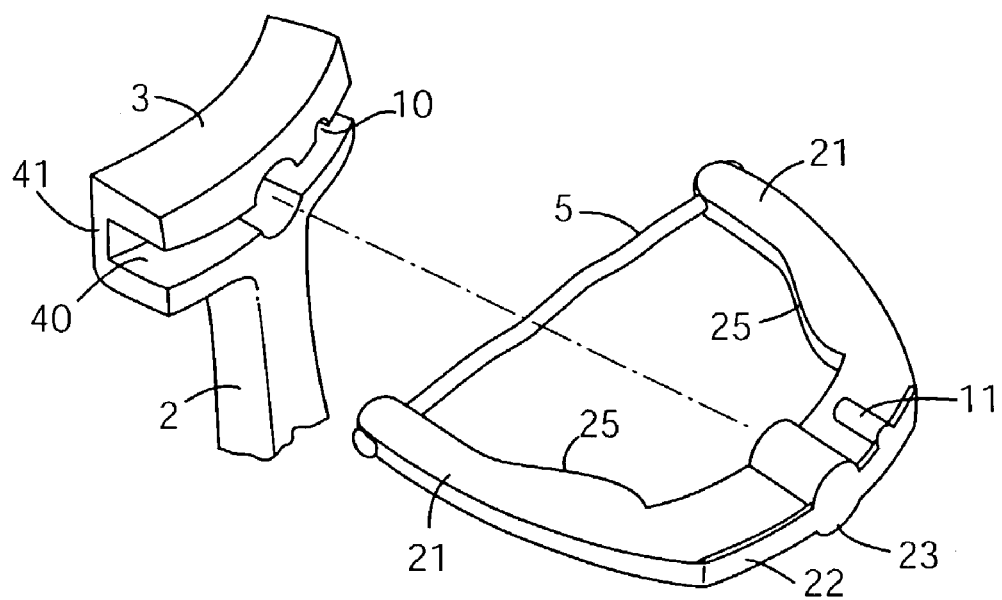
Figure 11:
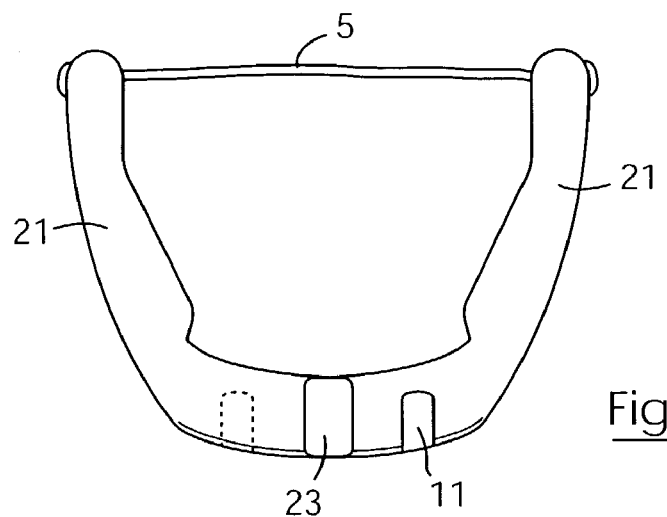
FIG. 11 is top plan view of the holder of FIG. 10.
Figure 12:
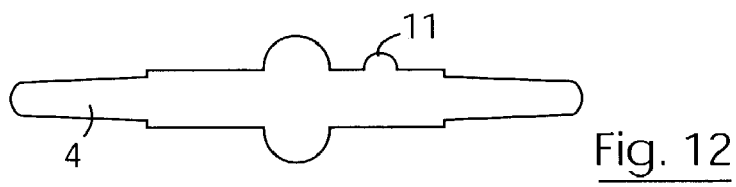
FIG. 12 is an end view of the holder of FIG. 10.
Figure 13:
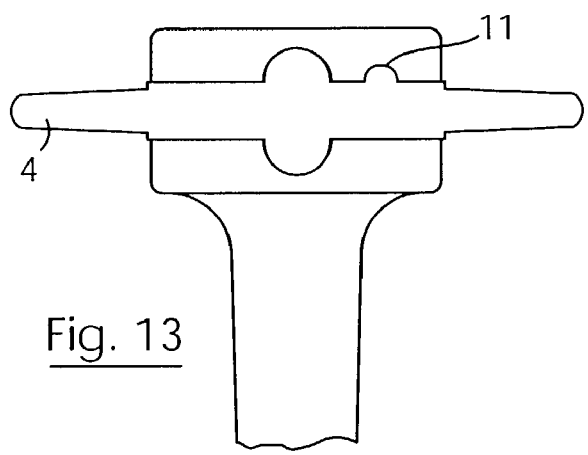
FIG. 13 is an end view of the holder of FIG. 10 mounted to a head piece.
Figure 10:
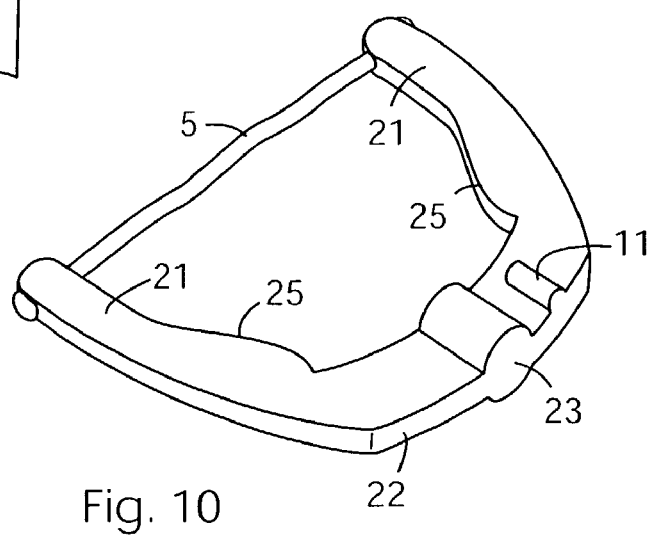
FIG. 10 is a perspective view of a holder part of the device of FIG. 9.
Figure 15:
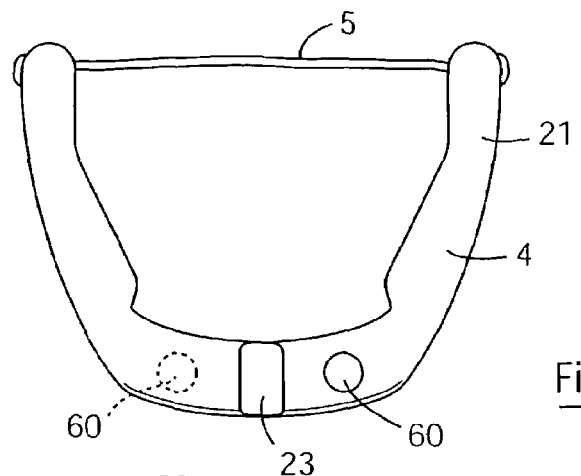
FIG. 15 is top plan view of the holder part of the device of FIG. 14.
Figure 16:
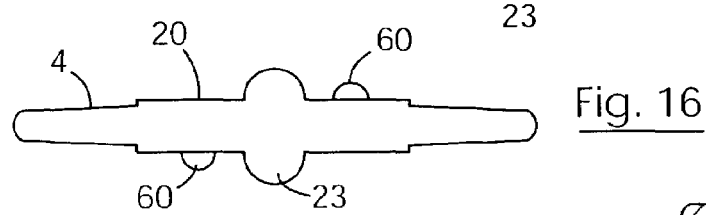
FIG. 16 is an end view of the holder part of the device of FIG. 14.
Figure 18:
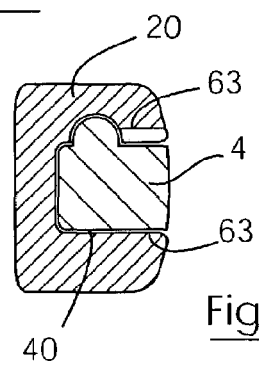
FIG. 18 is a cross sectional view of the device of FIG. 17 along the line indicated in FIG. 17.
Figure 17:
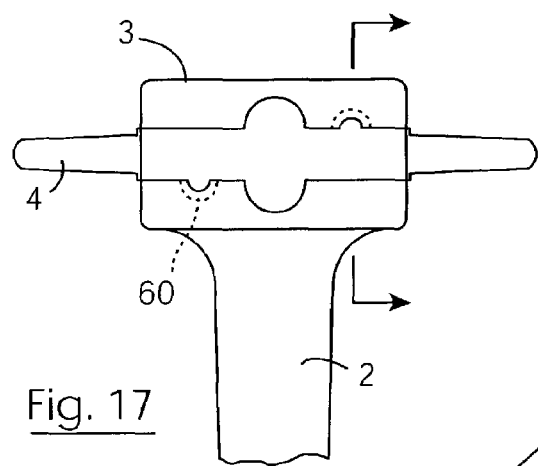
FIG. 17 is an end view of the holder part mounted to the head piece of the dental floss device of FIG. 14.
Figure 14:
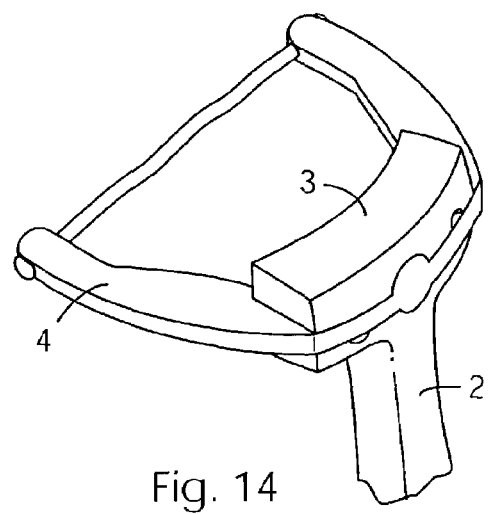
FIG. 14 is a perspective view of a dental floss holder part and a handle head piece part of another dental floss device of the invention.

Referring to FIG. 8 there is illustrated an alternative holder 50 in which a length of floss tape 51 extending between the jaws 21.

An alternative embodiment of the invention is illustrated in FIGS. 9 to 13 which is similar to that of FIGS. 1 to 7 and like parts are assigned the same reference numerals. In this case, there is only one interlock tongue 11 and interlock groove 10. There may also be two grooves 10 in the handle and one tongue 11 on the holder.

A further alternative embodiment of the invention is illustrated in FIGS. 14 to 22 which is similar to that of FIGS. 1 to 7 and like parts are assigned the same reference numerals.

In this case, there are two interlock receiving recesses 60 substantially hemispherical in shape in the engagement groove 40 of the holder 4. Corresponding substantially hemi-spherical projections 61 are located on the base portion 20 of the head piece 3. The head piece 3 may comprise only one corresponding projection 61.

The substantially hemi-spherical receiving recess 60 extends laterally to the edge 63 of the engagement groove 40. A laterally extending channel 62, extending from the receiving recess 60 to the edge 63 of the engagement groove 40, has a smaller radius than the radius of the receiving recess 60 as shown especially in FIGS. 17 to 19 and 21 and 22.

On assembly of the head piece 3 with the holder 4, the outer edges 63 of the engagement groove 40 deform slightly to allow the base portion 20 of the holder 4 with the hemi-spherical projections 61 to slidably engage with the corresponding laterally extending channel 62 of the receiving recess 60. The hemi-spherical projections 61 on the head piece 3 have a radius corresponding to the receiving recesses 60. The holder 4 is securely engaged with the head piece 3 when the hemi-spherical projections 61 snap-fittingly engage securely with the corresponding receiving recess 60. Such an engagement system ensures that the holder 4 is correctly aligned with the head piece 3.

The invention is not limited to the embodiments hereinbefore described which may be varied in detail.

The invention claimed is:

1. A dental floss device comprising:
a handle having a head piece; and
a dental floss holder for interengagement with the head piece;
the dental floss holder comprising a base portion and a pair of spaced-apart jaws extending from the base portion to accommodate a length of dental floss therebetween;

the jaws of the holder extending to embrace the head piece therebetween in a correct alignment configuration of the holder with respect to the handle; and said base portion including first and second lateral sides;

said head piece having an engagement groove including a first wall opposing a second wall;

an interlock comprising a tongue on one of the first lateral side of the base portion and the first wall of the engagement groove that fits into an interlock groove on the other of the first wall of the engagement groove and the first lateral side of the base portion, the engagement groove only accepting the base portion when the holder is inserted into the engagement groove with the first lateral side of said base portion facing the first wall of the head piece.

2. The device as claimed in claim 1 wherein the interlock is a push fit when the holder is in the correct alignment configuration.

3. The device as claimed in claim 1 wherein the interlock tongue is slidably engagable in the interlock groove when the holder is correctly aligned with the head piece.

4. The device as claimed in claim 1 wherein the interlock tongue is of arcuate shape in cross section and the interlock groove is of complementary arcuate shape.

5. The device as claimed in claim 1 wherein the interlock comprises a single head interlock part and a single holder interlock part.

6. The device as claimed in claim 1 wherein the interlock comprises at least two head interlock parts on the head piece and at least two holder interlock parts on the dental floss holder.

7. The device as claimed in claim 1 wherein the dental floss holder comprises a releasable lock for engagement on assembly with the head piece.

8. The device as claimed in claim 7 wherein the releasable lock comprises snap fit projections.

9. The device as claimed in claim 8 wherein the snap fit projections are provided on the jaws of the holder.

10. The device as claimed in claim 1 wherein the dental floss is a length of dental floss string.

11. The device as claimed in claim 1 wherein the dental floss is a length of dental floss tape.

12. A handle for a dental floss device as claimed in claim 1.

13. A dental floss holder for a dental floss device as claimed in claim 1.

14. A dental floss holder for assembly to a head piece of a handle, the dental floss holder comprising a base portion including first and second lateral sides and a pair of spaced-apart jaws extending from the base portion to accommodate a length of dental floss therebetween, the jaws of the holder extending to embrace a head piece of a handle therebetween in a correct alignment configuration of the holder with respect to a handle in use, the head piece having an engagement groove including a first wall opposing a second wall, the dental floss holder having a holder interlock comprising a tongue on one of the first lateral side of the base portion and the first wall of the engagement groove that fits into an interlock groove on the other of the first wall of the engagement groove and the first lateral side of the base portion, the engagement groove only accepting the base portion when the holder is inserted into the engagement groove with the first lateral side of the base portion facing the first wall of the head piece.

* * * * *